United States Patent [19]

Alt

[11] 4,155,744
[45] May 22, 1979

[54] HERBICIDAL α-HALOACETAMIDES

[75] Inventor: Gerhard H. Alt, Creve Coeur, Mo.

[73] Assignee: Monsanto Company, St. Louis, Mo.

[21] Appl. No.: 899,441

[22] Filed: Apr. 24, 1978

Related U.S. Application Data

[63] Continuation-in-part of Ser. No. 807,604, Jun. 17, 1977, abandoned.

[51] Int. Cl.$^2$ .................. A01N 9/28; C07D 307/22; C07D 307/14; C07D 307/52
[52] U.S. Cl. ........................... 71/88; 71/90; 260/332.2 R; 260/333; 260/338; 260/340.6; 260/340.7; 260/340.9 R; 260/345.7 R; 260/345.8 R; 260/347.2; 260/347.3; 260/347.4; 260/347.5; 260/348.43; 260/348.45; 260/348.46
[58] Field of Search ............... 260/347.2, 347.3, 347.5, 260/333, 338, 340.6, 340.7, 340.9 R, 345.7 R, 345.8 R, 347.4, 348.43, 348.45, 348.46; 71/88

[56] References Cited

U.S. PATENT DOCUMENTS

| | | | |
|---|---|---|---|
| 3,311,642 | 3/1967 | Marco et al. | 260/345.7 R |
| 3,819,661 | 6/1974 | Maravetz | 260/347.3 |
| 4,021,224 | 5/1977 | Pallos et al. | 71/88 |
| 4,113,464 | 9/1978 | Stach et al. | 71/88 |
| 4,116,670 | 9/1978 | Stach et al. | 71/88 |

FOREIGN PATENT DOCUMENTS 2135623 1/1973 Fed. Rep. of Germany .... 260/345.7 R

*Primary Examiner*—Richard Raymond
*Attorney, Agent, or Firm*—William I. Andress; Donald W. Peterson

[57] ABSTRACT

The disclosure herein relates to α-chloroacetamides substituted on the amide nitrogen atom with certain cycloalken-1-yl and heterocyclic radicals. These acetamides are useful as herbicides.

30 Claims, No Drawings

HERBICIDAL α-HALOACETAMIDES

CROSS REFERENCE TO RELATED APPLICATION

This application is a continuation-in-part of U.S. application Ser. No. 807,604, filed June 17, 1977, now abandoned.

BACKGROUND OF THE INVENTION

1. Field of the Invention

The invention herein pertains to the field of herbicides. More particularly, the field of this invention pertains to the use of α-haloacetamides as herbicides.

2. Description of the Prior Art

It is known in the prior art to use various α-haloacetamides as herbicides, either individually or in combination with other herbicides.

Among herbicidal compounds of the prior art are those acetamides having in varying arrangements substitutions of alkyl, cycloalkyl, alkenyl, cycloalkenyl, alkoxy, halogen, aryl, etc. groups, all of which may be further substituted with other radicals.

Illustrative of the 2-haloacetamides of the prior art and of those most closely related to the 2-haloacetamides disclosed and claimed herein are the α-haloacetamides disclosed in U.S. Pat. Nos. 3,495,967, 3,574,746, 3,586,496, 3,901,917, 3,819,661, 3,946,045 and 4,012,222. In the '967 patent the 2-chloroacetamides are characterized by substitutions on the nitrogen atom including a benzothiophene radical which may have other substituents. The '746 and '496 patents are directed generally to the same 2-haloacetamides which are characterized by a $C_{5-7}$ cycloalken-1-yl group and other substituents on the amide nitrogen. The '917 patent relates to 2-haloacetanilides characterized in having a thienylmethylene group which may be substituted with a lower alkyl group substituted on the nitrogen atom and the '661 patent relates to 2-haloacetanilides which are substituted with a furfuryl or tetrahydrofurfuryl. The '045 and '222 patents disclose α-haloacetanilides characterized by a dioxolanyl-lower alkyl group on the anilide nitrogen atom.

As will be apparent, the most relevant 2-haloacetamides of the prior art have either a heterocyclic or cycloalkenyl group attached to acetamide or acetanilide nitrogen atom, but not both radicals simultaneously — a feature which characterizes the 2-haloacetamides of the present invention and distinguishes them from the prior art.

SUMMARY OF THE INVENTION

The present invention relates to herbicidally active compounds, herbicidal compositions containing these compounds and herbicidal method of use of said compositions in agricultural crops, e.g., in dicotyledonous crops such as sugar-beets and soybeans and in monocotyledonous crops such as wheat, sorghum and rice.

The herbicidal compounds of this invention are characterized by the formula

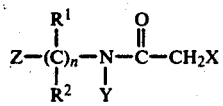

wherein

X is a halogen (Cl, Br, F or I);

Y is a $C_{5-7}$ cycloalken-1-yl or cycloalkadienyl radical;

Z is a saturated or unsaturated heterocyclic radical having up to 6 ring atoms containing O, $S(O)_m$ or NR groups;

m and n are 0, 1 or 2;

Y and Z may be unsubstituted or independently substituted with $C_{1-10}$ alkyls, especially lower alkyls, e.g., $C_{1-5}$ alkyls; $C_{2-8}$ alkenyls and alkynyls, especially $C_{2-6}$ alkenyls; $C_{1-8}$ alkoxys; $C_{1-12}$ alkoxyalkyls or polyalkoxys, especially those having up to $C_6$ atoms; $C_{5-7}$ cycloalkyls, cycloalkenyls or cycloalkadienyls; $C_{5-6}$ O, S or N-heterocyclics, halogen, $NO_2$, $CF_3$, cyano, hydroxy, lower alkylthio, carboloweralkoxy, phenyl, benzyl or up to 4 carbon atom alkenylene or alkylene groups forming a ring therewith;

R is hydrogen or a Y or Z group and $R^1$ and $R^2$ are hydrogen or $C_{1-6}$ alkyl or alkenyl groups.

The above compounds are used singly or in combination as the active ingredient(s) in herbicidal compositions to control undesirable vegetation in important crops.

DESCRIPTION OF PREFERRED EMBODIMENTS

The compounds according to this invention are suitably prepared by reacting the appropriate cyclohexylideneimine or N-cyclohexen-1-yl amine with a haloacylating agent. The starting imine or amine is suitably prepared by reacting the appropriately substituted cyclic ketone with the appropriately-substituted heterocyclic amine. If the starting cyclic ketone has a substituent, e.g., cyano or carboalkoxy, in the ortho position which conjugates with the ring the product will be an amine; otherwise, an imine.

In specific working embodiments, the preparation of exemplary compounds of this invention will be described in Example 1 below; the same general procedure was followed in order to prepare the compounds of Examples 2–16, but substituting the appropriate starting materials, solvents, reaction conditions, etc. required to obtain the designated product of each example.

EXAMPLE 1

This example describes the preparation of N-(furfuryl)-N-(2,6-dimethyl-1-cyclohexen-1-yl)-α-chloroacetamide.

0.1 mol of 2,6-dimethylcyclohexanone and 0.1 mol of furfurylamine in toluene were heated with 2 drops of methanesulfonic acid and the mixture refluxed under a Dean and Stark water separator until no more water was collected. The solvent was removed in vacuo and the residue distilled in vacuo using a short path vigreaux column. The product had a boiling point of 94°–95° C./0.8 mm. and was identified as N-furfuryl-2,6-dimethylcyclohexylideneimine.

The above imine (0.03 ml) in toluene (25 ml) was added to a solution of chloroacetyl chloride (0.033 mol) in toluene (25 ml). The reaction mixture was heated at reflux for 8 hours, during which time hydrogen chloride was evolved. The solvent was stripped in vacuo and the residue distilled under reduced pressure through a short path distillation apparatus. The product was recovered in 88% yield and had a boiling point of 154° C./0.4 mm.

| Analysis | | |
|---|---|---|
| Element | Calculated | Found |
| C | 63.84 | 63.65 |
| H | 7.15 | 7.12 |
| N | 4.97 | 4.88 |
| Cl | 12.58 | 12.68 |

The product was identified as the compound in the lead sentence of this example.

EXAMPLES 2–16

Following the same general procedure described in Example 1, but substituting the appropriate starting materials and reaction conditions, the compounds listed in Table 1 were prepared and had the physical properties shown for the respective compounds.

TABLE I

| Example No. | Compound | Empirical Formula | B.P. °C. (mm Hg) | Element | Analysis Calculated | Found | Yield % |
|---|---|---|---|---|---|---|---|
| 2 | N-(furfuryl-N-1(3,4-dihydro-naphthyl)-α-chloroacetamide | $C_{17}H_{16}ClNO_2$ | 203-05 (0.3) | C | 67.66 | 67.37 | 78 |
| | | | | H | 5.34 | 5.42 | |
| | | | | Cl | 11.75 | 11.82 | |
| | | | | N | 4.64 | 4.54 | |
| 3 | N-(tetrahydrofurfuryl)N-(3,4-dihydro-1-naphthyl)-α-chloroacetamide | $C_{17}H_{20}ClNO_2$ | 221-22 (0.5) | C | 66.77 | 66.72 | 87 |
| | | | | H | 6.59 | 6.63 | |
| | | | | Cl | 11.59 | 11.54 | |
| | | | | N | 4.58 | 4.58 | |
| 4 | N-(furfuryl)-N-(2-furfuryl-6-methyl-1-cyclohexen-1-yl)-α-chloroocetamide in 70/30% admixture with the N-(furfuryl)-N-(2-methyl-6-furfuryl-1-cyclohexen-1-yl)-αchloroacetamide isomer thereof | $C_{19}H_{22}ClNO_3$ | 202-04 (0.5) (solidifies on standing M.P. 75-80) | C | 65.61 | 65.31 | 58 |
| | | | | H | 6.38 | 6.46 | |
| | | | | Cl | 10.19 | 10.27 | |
| | | | | N | 4.03 | 4.02 | |
| 5 | N-(tetrahydrofurfuryl)-N-(2,6-dimethyl-1-cyclohexen-1-yl)-α-chloroacetamide | $C_{15}H_{24}ClNO_2$ | 160-2 (0.2) | C | 63.03 | 62.78 | 81 |
| | | | | H | 8.56 | 8.49 | |
| | | | | N | 4.90 | 4.87 | |
| | | | | Cl | 12.41 | 12.51 | |
| 6 | N-(furfuryl)N-(2-methyl-3,4-dihydro-1-naphthyl-α-chloroacetamide | $C_{18}H_{18}ClNO_2$ | 90-92 (M.P.) | C | 68.46 | 68.47 | 74 |
| | | | | H | 5.75 | 5.76 | |
| | | | | Cl | 11.23 | 11.29 | |
| | | | | N | 4.44 | 4.51 | |
| 7 | N-(furfuryl)-N-(2-methyl-1-cyclohexen-1-yl)-α-chloroacetamide | $C_{14}H_{18}ClNO_2$ | 146-48 (0.2) | C | 62.80 | 62.57 | 73 |
| | | | | H | 6.77 | 6.80 | |
| | | | | Cl | 13.24 | 13.31 | |
| | | | | N | 5.23 | 5.30 | |
| 8 | N-(furfuryl)-N-(2-isopropyl-1-cyclohexen-1-yl)-α-chloroacetamide | $C_{16}H_{22}ClNO_2$ | 167 (0.7) | C | 64.94 | 64.71 | 88 |
| | | | | H | 7.50 | 7.57 | |
| | | | | Cl | 11.99 | 12.15 | |
| | | | | N | 4.74 | 4.71 | |
| 9 | N-(furfuryl)-N-(2-carboxyethyl-1-cyclohexen-1-yl)-α-chloroacetamide | $C_{16}H_{20}ClNO_4$ | 186-88 (0.8) | C | 58.99 | 58.90 | 58 |
| | | | | H | 6.19 | 6.20 | |
| | | | | Cl | 10.88 | 10.79 | |
| | | | | N | 4.30 | 4.30 | |
| 10 | N-(furfuryl)-N-(2-isopropyl-5-methyl-1-cylcohexen-1-yl)-α-chloroacetamide | $C_{17}H_{24}ClNO_2$ | 149-51 (0.2) | C | 65.90 | 65.72 | 81 |
| | | | | H | 7.87 | 7.82 | |
| | | | | Cl | 11.44 | 11.48 | |
| | | | | N | 4.52 | 4.51 | |
| 11 | N-(furfuryl)-N-(1-cyclohexen-1-yl)-α-chloroacetamide | $C_{13}H_{16}ClNO_2$ | 141 (0.3) | C | 61.54 | 61.40 | 64 |
| | | | | H | 6.36 | 6.36 | |
| | | | | Cl | 13.97 | 14.03 | |
| | | | | N | 5.52 | 5.53 | |
| 12 | N-(2-tetrahydropyranylmethyl)-2-methyl-1-cyclohexen-1-yl-α-chloroacetamide | $C_{15}H_{24}ClNO_2$ | 149-50 (0.15) | C | 63.03 | 62.66 | 80 |
| | | | | H | 8.46 | 8.25 | |
| | | | | Cl | 12.41 | 12.89 | |
| | | | | N | 4.90 | 4.99 | |
| 13 | N-(2-tetrahydropyranylmethyl)-2,6-dimethyl-1-cyclohexen-1-yl-α-chloroacetamide | $C_{16}H_{26}ClNO_2$ | 153-54 (0.2) | C | 64.09 | 63.80 | 82 |
| | | | | H | 8.74 | 8.72 | |
| | | | | Cl | 11.82 | 11.68 | |
| | | | | N | 4.67 | 4.68 | |
| 14 | N-(furfuryl)-N-1-cyclohepten-1-yl-α-chloroacetamide | $C_{14}H_{18}ClNO_2$ | 151-52 (0.4) | C | 62.80 | 62.84 | 79 |
| | | | | H | 6.18 | 6.23 | |
| | | | | Cl | 13.24 | 13.41 | |
| | | | | N | 5.23 | 5.21 | |
| 15 | N-(thenyl)-2,6-dimethyl- | $C_{15}H_{20}ClNOS$ | 168 | C | 60.49 | 59.94 | 86 |

TABLE I-continued

| Example No. | Compound | Empirical Formula | B.P. °C. (mm Hg) | Analysis Element | Calculated | Found | Yield % |
|---|---|---|---|---|---|---|---|
| | 1-cyclohexen-1-yl-α-chloroacetamide | | (0.15) | H | 6.77 | 6.57 | |
| | | | | Cl | 11.90 | 12.30 | |
| | | | | N | 4.70 | 4.79 | |
| 16 | N-(furfuryl)-N-1-(octa-hydronaphthyl)-α-chloroacetamide | $C_{17}H_{22}ClNO_2$ | 169–70 (0.05) | C | 66.33 | 66.60 | 77 |
| | | | | H | 7.30 | 6.92 | |
| | | | | Cl | 11.52 | 11.87 | |
| | | | | N | 4.55 | 4.65 | |

EXAMPLE 17

This example describes the preparation of N-(furfuryl)-N-(2-isopropylthio-1-cyclohexen-1-yl)-α-chloroacetamide.

To a solution of 0.033 mol of chloroacetyl chloride in 50 mls of cold toluene was added with stirring and cooling a solution of 0.03 mol N-furfuryl-2-isopropylthiocyclohexylidineimine (prepared from furfuryl amine and 2-isopropylthiocycloxanone according to the general procedure discussed above) in 30 ml of toluene. The reaction mixture was stirred for one hour at room temperature. 0.035 mol of triethylamine was then added and stirring continued an additional hour. The reaction mixture was then washed twice with 20 mls of water, dried over $MgSO_4$ and evaporated. The residual oil was stripped in high vacuum for 24 hours to obtain the compound in the lead sentence of this example in 92% yield.

| Analysis ($C_{16}H_{20}ClNO_2S$) | | |
|---|---|---|
| Element | Calculated | Found |
| C | 58.61 | 58.48 |
| H | 6.76 | 6.84 |
| Cl | 10.81 | 11.11 |
| N | 4.27 | 4.40 |

EXAMPLE 18

This example describes the preparation of N-(furfuryl)-N-(2,5-dimethyl-1-cyclopenten-1-yl)-α-chloroacetamide by the chloroacetylation of the corresponding imine starting material.

2,5-Dimethylcyclopentanone (5.73 g, 0.05 mol) and furfurylamine (6.39 g; 0.0625 mol) in toluene (70 ml) were heated at the reflux temperature under a Dean and Stark water separator until the theoretical amount of water (0.9 ml) was collected (6 days). The solvent was stripped in vacuo and the residual oil (10.81 g) subjected to vacuum distillation. The product, N-(furfuryl)-2,5-dimethylcyclopentylidenimine, had b.p. 78°–79.5°/0.05 mm (8.96 g).

The above imine (8.9 g; 0.047 mol) in toluene (30 ml) was added dropwise to a cooled and stirred solution of chloroacetyl chloride (5.94 g; 0.0515 mol) in toluene (40 ml). When the addition was complete the reaction mixture was stirred for 30 minutes and triethylamine (5.22 g; 0.052 mol) added. The reaction mixture was stirred at room temperature for 2 hours. Water (100 ml) was then added and the layers separated. The toluene layer was washed with water, dried with magnesium sulfate and evaporated in vacuo. The residual orange-red oil (11.1 g was purified by Kugelrohr distillation to give 6.33 g product as named in the lead sentence of this example.

Calc'd for $C_{14}H_{18}ClNO_2$ (percent) C, 62.80; H, 6.78; Cl, 13.24; N, 5.23 Found: C, 59.13; H, 6.36; Cl, 12.62; N, 4.95.

Following essentially the identical procedure described in Example 18, but substituting the appropriate starting materials, other N-cyclopenten-1-yls are prepared as exemplified by N-(tetrahydrofurfuryl)-N-(2,5-dimethyl-1-cyclopenten-1-yl)-α-chloroacetamide (a pale amber liquid, b.p. 140°–143°/0.15–0.2 mm); N-(2-pyranyl)-N-(2,5-dimethyl-1-cyclopenten-1-yl)-α-chloroacetamide and the dihydropyranyl and tetrahydropyranyl analogs thereof; N-(furfuryl)-N-(2-methyl-1-cyclopenten-1-yl)-α-chloroacetamide, N-(2-pyranyl)-N-(2-methyl-1-cyclopenten-1-yl)-α-chloroacetamide.

As indicated earlier herein, other alkyl groups may be substituted on either or both of the heterocyclic and/or cyclopenten-1-yl moieties of these α-haloacetamides.

EXAMPLE 19

Pre-emergent herbicidal activity of representative compounds of this invention is determined by the following procedure:

A good graph of top soil is placed in aluminum pans and compacted to a depth of 9.5 to 11.3 mm from the top of the pan. A predetermined number of seeds or vegetative propagules of each of several test plant species are placed on top of the soil in the pans and pressed into the soil surface. The amount of soil required to fill these pans after planting the seeds is weighed into similar pans. A known amount of active ingredient, applied in a solvent or as a wettable powder, is thoroughly mixed with the soil and used as a cover layer for the seeds planted in the pans. The pans are then placed on a sand bench in the greenhouse and watered from below as needed. The plants are observed at the end of approximately 14 days and the results recorded.

The pre-emergent phytotoxic activity of the compounds is measured in herbicidal ratings. The herbicidal rating is obtained by means of a fixed scale based on the percent control of each test species as follows:

| Percent Control | | Herbicidal Rating |
|---|---|---|
| 0 – 24 | = | 0 |
| 25 – 49 | = | 1 |
| 50 – 74 | = | 2 |
| 75 – 100 | = | 3 |

The pre-emergent phytotoxic activities of some of the compounds of this invention are summarized in Table 2. A dash (—) denotes that the species is not in the test or was not tested at a given rate. The herbicidal solutions used herein were applied at the indicated application rates expressed in terms of kg/ha.

Table 2

Pre-emergence Herbicidal Activity

| Compound of Ex. | Rate Kg/Hg | Soybean | Sugar-beet | Wheat | Rice | Sorghum | Cockle-bur | Wild Buck-wheat | Morning-glory | Hemp Sesbania | Lambs-quarters | Smart-weed | Velvet-leaf | Downy Brome | Panicum Spp. | Barn-yard-grass | Crab-grass | Canada Thistle | Nut-sedge | Quack-grass | Johnson-grass |
|---|---|---|---|---|---|---|---|---|---|---|---|---|---|---|---|---|---|---|---|---|---|
| 1 | 5.60 | 1 | 2 | 3 | 3 | 3 | 1 | 0 | 1 | 3 | 3 | 3 | 1 | 3 | 3 | 3 | 3 | 1 | 3 | 3 | 2 |
|   | 1.12 | 0 | 1 | 3 | 3 | 3 | 0 | 0 | 1 | 1 | 3 | 2 | 1 | 3 | 3 | 3 | 3 | — | — | — | — |
|   | 0.28 | 1 | 0 | 0 | 2 | 0 | 0 | 0 | 0 | 1 | 1 | 1 | 0 | 1 | 2 | 2 | 3 | — | — | — | — |
| 2 | 5.60 | 1 | 0 | 0 | 2 | 0 | 0 | 0 | 1 | 1 | 0 | 0 | 0 | 0 | 0 | 1 | — | — | — | — | — |
|   | 1.12 | 1 | 0 | 0 | 2 | 0 | 0 | 0 | 1 | 0 | 0 | 0 | 0 | 0 | 0 | — | — | — | — | — | — |
| 3 | 11.2 | — | — | — | — | — | 0 | — | 0 | — | 0 | 0 | 0 | 3 | 3 | 3 | 3 | — | — | 0 | 0 |
| 4 | 11.2 | — | — | — | — | — | 0 | — | 1 | — | 0 | 2 | 0 | 3 | 2 | 2 | — | — | — | 1 | 3 |
| 5 | 11.2 | 1 | 2 | 1 | 2 | 1 | 0 | 0 | 1 | 1 | 1 | 1 | 0 | 3 | 3 | 3 | 3 | 1 | 3 | 2 | 3 |
|   | 5.60 | 1 | 1 | 1 | 3 | 0 | 0 | 0 | 0 | 1 | 3 | 1 | 0 | 3 | 3 | 3 | 3 | 0 | 3 | 1 | 1 |
|   | 1.12 | 1 | 0 | 0 | 0 | 0 | 0 | 0 | 0 | 2 | 3 | 2 | 0 | 3 | 2 | 2 | 2 | 1 | 3 | 2 | 3 |
|   | 0.28 | 0 | 0 | 0 | 0 | 0 | 0 | 0 | 0 | 0 | 2 | 1 | 0 | 2 | 2 | 3 | 2 | 1 | 1 | 1 | 1 |
| 6 | 11.2 | 1 | 2 | 2 | 2 | 3 | 0 | 0 | 0 | 0 | 0 | 0 | 0 | 2 | 3 | 3 | — | 0 | 3 | 2 | — |
|   | 5.60 | 0 | 1 | 0 | 1 | 1 | 0 | 0 | 0 | 0 | 0 | 1 | 0 | 0 | 0 | 0 | 0 | — | — | — | — |
|   | 1.12 | 1 | 0 | 0 | 0 | 0 | 0 | 0 | 0 | 0 | 0 | 0 | 0 | 0 | 0 | 0 | 0 | — | — | — | — |
|   | 0.28 | 0 | 0 | 0 | 0 | 0 | 0 | 0 | 0 | 0 | 0 | 0 | 0 | 0 | 0 | 0 | 0 | 0 | 0 | 0 | 0 |
| 9 | 11.2 | 0 | 0 | 2 | 2 | 2 | 0 | 0 | 0 | 2 | 0 | 0 | 0 | 2 | 3 | 3 | 3 | — | 3 | 2 | 3 |
|   | 5.60 | 1 | 1 | 0 | 0 | 0 | 0 | 0 | 0 | 0 | 2 | 0 | 0 | 0 | 3 | 3 | 2 | — | 1 | 1 | — |
|   | 1.12 | 0 | 0 | 0 | 0 | 0 | 0 | 0 | 0 | 0 | 0 | 0 | 0 | 0 | 0 | 0 | 0 | 0 | 0 | 0 | 0 |
| 10 | 11.2 | — | 1 | 0 | 3 | 1 | 1 | 1 | 0 | 0 | 0 | 0 | 1 | 2 | 3 | 3 | 3 | 1 | 3 | 2 | 0 |
|   | 5.60 | 0 | 0 | 0 | 0 | 0 | 0 | 0 | 0 | 0 | 0 | 0 | 0 | 2 | 2 | 3 | — | — | — | — | — |
|   | 1.12 | — | — | — | — | — | 0 | 0 | 0 | 0 | 0 | 0 | 0 | 3 | 3 | 3 | 3 | 0 | 3 | 2 | 3 |
|   | 0.28 | 0 | 0 | 0 | 0 | 0 | 0 | 0 | 0 | 0 | 0 | 0 | 0 | 1 | 1 | 3 | 2 | — | — | — | — |
| 11 | 11.2 | 0 | 0 | 2 | 2 | 2 | 0 | 0 | 0 | 0 | 2 | 2 | 0 | 2 | 3 | 3 | 3 | 1 | 3 | 3 | 1 |
|   | 5.60 | 0 | 0 | 0 | 0 | 0 | 0 | 2 | 0 | 0 | 0 | 0 | 0 | 1 | 2 | 3 | 3 | — | — | — | — |
|   | 1.12 | — | — | — | — | — | 1 | 0 | 0 | 0 | 3 | 0 | 0 | 3 | 3 | 3 | 3 | 2 | 1 | 2 | 0 |
|   | 0.28 | 0 | 0 | 0 | 0 | 0 | 0 | 0 | 0 | 0 | 2 | 0 | 0 | 2 | 3 | 3 | 3 | — | — | — | — |
| 13 | 11.2 | — | 3 | 2 | 3 | 3 | 0 | 1 | 0 | 0 | 3 | 2 | 0 | 3 | 3 | 3 | 3 | — | 3 | 3 | — |
|   | 5.60 | 0 | 2 | 1 | 2 | 2 | 0 | 0 | 0 | 0 | 2 | 1 | 0 | 2 | 2 | 3 | 3 | — | 1 | 1 | 0 |
|   | 1.12 | 0 | 0 | 0 | 0 | 0 | 0 | 0 | 0 | 0 | 0 | 0 | 0 | 0 | 0 | 0 | 0 | — | — | — | — |
|   | 0.28 | 0 | 0 | 0 | 0 | 0 | 0 | 0 | 0 | 0 | 0 | 0 | 0 | 0 | 0 | 0 | 0 | 0 | 0 | 0 | 0 |
| 14 | 11.2 | — | 0 | 1 | 3 | 3 | 0 | 1 | 0 | — | 0 | 0 | 0 | 3 | 3 | 3 | 3 | — | 2 | 2 | 1 |
|   | 5.60 | 0 | 0 | 0 | — | 0 | 0 | 0 | 0 | 0 | 0 | 0 | 0 | 3 | 2 | 3 | 3 | — | — | — | — |
|   | 1.12 | 0 | 0 | 0 | 1 | 0 | 0 | 0 | 0 | 0 | 0 | 0 | 0 | 3 | 3 | 3 | 3 | 1 | 3 | 2 | 1 |
|   | 0.28 | — | — | — | — | — | 0 | 0 | 0 | 0 | 0 | 0 | 0 | 0 | 0 | 2 | 2 | — | — | — | — |
| 15 | 11.2 | 0 | 0 | 2 | 2 | 2 | 0 | 0 | 0 | 0 | 3 | 2 | 0 | 3 | 3 | 3 | 3 | — | 3 | 2 | 0 |
|   | 5.60 | 0 | 0 | 0 | 0 | 0 | 0 | 0 | 0 | 0 | 0 | 0 | 0 | 2 | 2 | 3 | — | — | — | — | — |
|   | 1.12 | 0 | 0 | 0 | 1 | 0 | 0 | 0 | 0 | 0 | 0 | 0 | 0 | 0 | 0 | 2 | 2 | 0 | — | 0 | 0 |
|   | 0.28 | 0 | 0 | 0 | 0 | 0 | 0 | 0 | 0 | 0 | 0 | 0 | 0 | 0 | 0 | 0 | 0 | 0 | 0 | 0 | 0 |
| 16 | 11.2 | 0 | 0 | 1 | 2 | 2 | 0 | 0 | 0 | 0 | 0 | 0 | 0 | 3 | 2 | 3 | 3 | — | 2 | 2 | 0 |
|   | 5.60 | 0 | 0 | 0 | 0 | 0 | 0 | 0 | 0 | 0 | 0 | 0 | 0 | 2 | 0 | 2 | 2 | — | — | — | — |
|   | 1.12 | 0 | 0 | 0 | — | 0 | 0 | 0 | 0 | 0 | 0 | 0 | 0 | 0 | 0 | 0 | 0 | 0 | 0 | 0 | 0 |
|   | 0.28 | 0 | 0 | 0 | — | 0 | 0 | 0 | 0 | 0 | 0 | 0 | 0 | 0 | 0 | 0 | 0 | 0 | 0 | 0 | 0 |
| 17 | 56.0 | — | — | — | — | — | — | — | — | — | — | — | — | — | — | — | — | — | — | — | — |
|   | 28.0 | — | — | — | — | — | 0 | 0 | 0 | 0 | 0 | 0 | 0 | 2 | 2 | 3 | 2 | — | — | — | — |
|   | 11.2 | 0 | 0 | 3 | 3 | 3 | 0 | 0 | 0 | — | 3 | 3 | 0 | 3 | 3 | 3 | 3 | 3 | 3 | 3 | 0 |
| 18 | 5.60 | 0 | 0 | 2 | 2 | 0 | 0 | 0 | 0 | 0 | — | 3 | 1 | 3 | 3 | 3 | 3 | — | — | — | — |
|   | 1.12 | 0 | 0 | 0 | 0 | 0 | 0 | 0 | 1 | 0 | — | 1 | 0 | 1 | 0 | 3 | 1 | — | — | — | — |
|   | 0.28 | 0 | 0 | 0 | 0 | 0 | 0 | 0 | 0 | 0 | — | — | 0 | 0 | 0 | 3 | 0 | — | — | — | — |
|   | 0.06 | 0 | 0 | 0 | 0 | 0 | 0 | 0 | 0 | 0 | — | — | 0 | 0 | 0 | — | — | — | — | — | — |
|   | 0.01 | 0 | 0 | 0 | 0 | 0 | 0 | 0 | 0 | 0 | — | — | 0 | 0 | 0 | 1 | 0 | — | — | — | — |

In order to further illustrate the selective nature of preferred herbicides according to this invention, additional tests were conducted on wheat (Table 3) and sugarbeets (Table 4) and grass weeds commonly associated therewith. In Tables 3 and 4 the pre-emergence activity data is presented in terms of "Percent Inhibition" of the treated plants. The herbicides used in these tests were applied at the indicated concentrations in a volume of suitable solvent, e.g., acetone, corresponding to about 187 liters/hectare.

TABLE 3

Pre-emergence Activity
On Wheat and Grass Weeds
(Percent Inhibition)

| Compound of Ex. No. | Rate Kg/Ha. | Wheat | Wild Oats | Yellow Foxtail | Downy Brome | Black-grass |
|---|---|---|---|---|---|---|
| 1 | 1.12 | 75 | 95 | 100 | 100 | 100 |
|   | 0.56 | 60 | 85 | 100 | 100 | 95 |
|   | 0.28 | 55 | 85 | 100 | 95 | 95 |
|   | 0.14 | 20 | 75 | 100 | 85 | 85 |
| 5 | 1.12 | 50 | 95 | 100 | 100 | 95 |
|   | 0.56 | 10 | 85 | 100 | 95 | 70 |
|   | 0.28 | 0 | 20 | 95 | 50 | 60 |
|   | 0.14 | 0 | 0 | 85 | 0 | 0 |

Using 15% inhibition of growth or injury (i.e., $GR_{15}$) to the crop, wheat, and 85% inhibition of growth or injury ($GR_{85}$) to the weeds as a measure of acceptable potential commercial performance, it is noted that the compound of Example 1 controlled yellow foxtail, downy brome and blackgrass at each rate tested, but was still a little too toxic for use in wheat at 0.14 kg/ha. Accordingly, a lesser quantity of active ingredient, perhaps 0.7–0.10 kg/ha, would be required to achieve $GR_{15}$ in wheat and $GR_{85}$ in foxtail, brome and blackgrass.

The compound of Example 5 was safe on wheat at 0.56 kg/ha while controlling wild oats, yellow foxtail and downy brome. Increasing the rate of application to a level which would establish $GR_{15}$ (0.63 kg/ha by extrapolation) would probably achieve $GR_{85}$ in blackgrass.

The pre-emergence activity data for the compounds of Examples 1 and 5 in sugarbeets and weeds associated therewith is shown in Table 4.

TABLE 4

Pre-emergence Activity
On Sugarbeets and Grass Weeds

| Compound of Ex. No. | Rate Kg/Ha. | Sugarbeets | Wild Oats | Barnyard Grass | L. Crabgrass | Blackgrass | Yellow Foxtail |
|---|---|---|---|---|---|---|---|
| 1 | 1.12 | 15 | 95 | 100 | 100 | 100 | 100 |
|   | 0.56 | 5 | 90 | 100 | 100 | 95 | 100 |
|   | 0.28 | 0 | 85 | 100 | 100 | 85 | 95 |
|   | 0.14 | 0 | 30 | 95 | 85 | 70 | 90 |
| 5 | 1.12 | 20 | 90 | 100 | 100 | 95 | 100 |
|   | 0.56 | 5 | 70 | 95 | 90 | 60 | 90 |
|   | 0.28 | 0 | 20 | 75 | 75 | 40 | 85 |
|   | 0.14 | 0 | 0 | 85 | 40 | 20 | 80 |

It will be noted that the compound of Example 1 is safe on sugarbeets at 1.12 kg/ha while controlling each of the weeds associated therewith at an application rate of 0.28 kg/ha and barnyardgrass, crabgrass and yellow foxtail at 0.14 kg/ha. The compound of Example 5 was safe on sugarbeets and controlled barnyard grass, crabgrass and yellow foxtail at 0.56 kg/ha. At a higher rate of application (i.e., 0.93 kg/ha by extrapolation) required to reach $GR_{15}$ in sugarbeets, it is quite possible that $GR_{85}$ might also be attained in wild oats and blackgrass.

The selectivity of a herbicide may be evaluated by reference to a "selectivity factor" calculated as the ratio of $GR_{15}/GR_{85}$. For example, in Example 1 in Table 4, the $GR_{15}$ for sugarbeets is 1.12 kg/ha whereas the $GR_{85}$ for each of the weeds wild oats and blackgrass is 0.28 kg/ha. Accordingly, the selectivity factor for the compound of Example 1 in sugarbeets with respect to these weeds is about 4.0; with respect to crabgrass, the selectivity factor is about 8.0 and for barnyardgrass and yellow foxtail greater than 8.0.

The foregoing experimental data provides an indication of the efficacy of the invention compounds as selective herbicides, particularly with respect to grass weeds in dicotyledonous crops, e.g., sugarbeets and soybeans and in monocotyledons, e.g., cereal crops, esp. wheat, sorghum and rice.

The active ingredient herein can be admixed with one or more adjuvants which can be solid or liquid extenders, carriers, diluents, conditioning agents and the like to form herbicidal compositions. Herbicidal compositions containing the active ingredients of this invention can be formulated with or in the form of granules, wettable powders, aqueous suspensions, dust formulations, emulsifiable oils and solutions in solvents. In general, these formulations can all contain one or more surface-active agents.

Surface-active agents which can be used in herbicidal formulations are well known to those skilled in the art and have been well documented in patents, bulletins and textbooks.

The preparation, formulation and particle size of the granules, wettable powders, aqueous suspensions, dusts, emulsifiable oils and solutions in solvents are also well known to those skilled in the art and well documented.

The active ingredient is usually present in the herbicidal compositions in a range of about 0.5 to 95 parts by weight per 100 parts by weight of wettable powder and dust formulations and from about 5 to 95 parts by weight per 100 parts by weight emulsifiable oil formulations. Formulations containing more or less than the above quantities of active ingredient can easily be prepared by those skilled in the art.

The quantity of active ingredient to be used in the field may vary within certain limits depending upon variables known to those in the art, e.g., condition of the soil, climate, plants, etc. In general, however, amounts ranging from about 0.02 to 11.2 or more kg/ha should be adequate; a preferred range being from about 0.06 to 6.0 kg/ha or suitably, an amount within the range of from 0.25 to 4.0 kg/ha.

Modes of application of the herbicidal compositions of this invention to the plant are well known to those skilled in the art. The application of liquid and particulate solid herbicidal formulations to the above-ground portions of plants can be carried out by conventional methods, e.g., power dusters, boom and hand sprayers and spray dusters.

The phytotoxic compositions of this invention can also contain other additaments, for example, fertilizers, safening agents, other phytotoxicants, pesticides and the like, used as adjuvant or in combination with any of the above-described adjuvants.

The compounds of this invention may be used in combination with known herbicides in order to provide enhanced biological effectiveness. The use of various herbicides in combination at the time of a single application or sequentially is common in practice. Herbicides which may be used in combination with the compounds of this invention include but are not limited to:

Substituted phenoxyaliphatic acids such as 2,4-dichlorophenoxyacetic acid; 2,4,5-trichlorophenoxyacetic acid, 2-methyl-4-chlorophenoxyacetic acid and the salts, esters and amides thereof; symmetrical or asymmetrical triazine derivatives, such as 2-chloro-4-ethylamino-6-isopropylamino-s-triazine; 2,4-bis(isopropylamino)-6-methoxy-s-triazine and 2-methylmercapto-4,6-bis(isopropylamino)-s-triazine; urea derivatives such as 3-(3,4-dichlorophenyl)-1,1-dimethylurea and 3-(m-trifluoromethylphenyl)-1,1-dimethylurea and 3-(3,4-dichlorophenyl)-1-methoxy-1-methylurea; pyridylium derivatives such as 1:1'-ethylene-2,2'-dipyridylium dihalide; acetanilides such as N-isopropyl-α-chloroacetanilide, and 2-chloro-2',6'-diethyl-N-methoxymethyl acetanilide; acetamides such as N,N-diallyl-α-chloroacetamide, carbamates such as ethyl-N,N-di-n-propylthiolcarbamate, and 2,3-dichloroallyl diisopropylthiolcarbamate; substituted uracils such as 5-bromo-3-sec-butyl-6-methyluracil, substituted anilines such as N,N-dipropyl-α,α,α-trifluoro-2,6-dinitro-p-toluidine; pyridazone derivatives such as 5-amino-4-chloro-2-phenyl-3-(2H)-pyridazinone; diphenyl ethers which may be unsubstituted or substituted with halogen, nitro, hydroxy, alkylthio, trifluoromethyl, cyano, alkyl, alkoxy, etc. groups; benzothiadiazinone derivatives such as 3-isopropyl-(1H)-benzo-2,1,3-thiadiazin-4-one-2,2-dioxide; N-(phosphonomethyl)glycine and its $C_{1-6}$ monoalkyl amine and alkali metal salts and combinations thereof in ratios of 1–4 lb/acre (1.12–4.48 kg/ha) to 1–4 lb/acre of other herbicidal compounds, which may be selected from those exemplified above.

Fertilizers useful in combination with the active ingredients include, for example ammonium nitrate, urea and superphosphate. Other useful additaments include materials in which plant organisms take root and grow such as compost, manure, humus, sand and the like.

While the illustrative embodiments of the invention have been described hereinbefore with particularity, it will be understood that various other modifications will be apparent to and can readily be made by those skilled in the art without departing from the scope and spirit of the invention. Accordingly, it is not intended that the scope of the claims appended hereto be limited to the examples and description set forth herein but rather the claims be construed as encompassing all the features of patentable novelty which reside in the present invention including all features which would be treated as equivalents thereof by those skilled in the art to which the invention pertains.

I claim:

1. Compounds of the formula

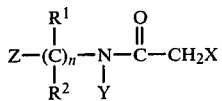

wherein
X is a halogen;
Y is a $C_{5-7}$ cycloalken-1-yl or cycloalkadienyl radical;
Z is a saturated or unsaturated heterocyclic radical having up to 6 ring atoms containing O;
n is 0, 1 or 2;
Y and Z may be unsubstituted or independently substituted with $C_{1-10}$ alkyl, $C_{2-8}$ alkenyl or alkynyl, $C_{1-8}$ alkoxy, $C_{2-12}$ alkoxyalkyl or polyalkoxy having up to 12 carbon atoms, $C_{5-7}$ cycloalkyl, cycloalkenyl or cycloalkadienyl, $C_{5-6}$ O-heterocyclyl, halogen, $NO_2$, $CF_3$, CN, OH, lower alkylthio, caboloweralkoxy, phenyl, benzyl or up to 4 carbon atom alkenylene or alkylene groups to form a ring therewith and
$R^1$ and $R^2$ are hydrogen or $C_{1-6}$ alkyl or alkenyl groups.

2. Compounds according to claim 1 wherein Y is a $C_{5-7}$ cycloalken-1-yl which may be substituted with any of said groups.

3. Compounds according to claim 2 wherein said cycloalken-1-yl is substituted with lower alkyl.

4. Compounds according to claim 3 wherein said alkyl-substituted cycloalken-1-yl is 2,6-di-loweralkylcyclohexen-1-yl.

5. Compounds according to claim 1 wherein n is 1 and Z is furyl.

6. Compounds according to claim 1 wherein n is 1 and Z is tetrahydrofuryl.

7. Compound accordiing to claim 1 which is N-(furfuryl)-N-(2,6-dimethyl-1-cyclohexen-1-yl)-α-chloroacetamide.

8. Compound according to claim 1 which is N-(tetrahydrofurfuryl)-N-(2,6-dimethyl-1-cyclohexen-1-yl)-α-chloroacetamide.

9. Compound according to claim 1 which is N-(furfuryl)-N-(2,5-dimethyl-1-cyclopenten-1-yl)-α-chloroacetamide.

10. Compound according to claim 1 which is N-(tetrahydrofurfuryl)-N-(2,5-dimethyl-1-cyclopenten-1-yl)-α-chloroacetamide.

11. Herbicidal compositions comprising a herbicidally efffective amount of a compound of the formula

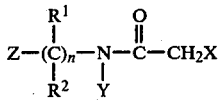

wherein
X is a halogen;
Y is a $C_{5-7}$ cycloalken-1-yl or cycloalkadienyl radical;
Z is a saturated or unsaturated heterocyclic radical having up to 6 ring atoms containing O;
n is 0, 1 or 2;
Y and Z may be unsubstituted or independently substituted with $C_{1-10}$ alkyl, $C_{2-8}$ alkenyl or alkynyl, $C_{1-8}$ alkoxy, $C_{2-12}$ alkoxyalkyl or polyalkoxy, $C_{5-7}$ cycloalkyl, cycloalkenyl or cycloalkadienyl, $C_{5-6}$ O-heterocyclyl, halogen, $NO_2$, $CF_3$, CN, OH, lower alkylthio, caboloweralkoxy, phenyl, benzyl or up to 4 carbon atom alkenylene or alkylene groups to form a ring therewith and
$R^1$ and $R^2$ are hydrogen or $C_{1-6}$ alkyl or alkenyl groups.

12. Compositions according to claim 11 wherein Y is a $C_{5-7}$ cycloalken-1-yl which may be substituted with any of said groups.

13. Compositions according to claim 12 wherein said cycloalken-1-yl is substituted with lower alkyl.

14. Compositions according to claim 13 wherein said alkyl-substituted cycloalken-1-yl is 2,6-di-loweralkylcyclohexen-1-yl.

15. Compositions according to claim 11 wherein n is 1 and Z is furyl.

16. Compositions according to claim 11 wherein n is 1 and Z is tetrahydrofuryl.

17. Composition according to claim 11 wherein said compound is N-(furfuryl)-N-(2,6-dimethyl-1-cyclohexen-1-yl)-α-chloroacetamide.

18. Composition according to claim 11 wherein said compound is N-(tetrahydrofurfuryl)-N-(2,6-dimethyl-1-cyclohexen-1-yl)-α-chloroacetamide.

19. Composition according to claim 11 wherein said compound is N-(furfuryl)-N-(2,5-dimethyl-1-cyclopenten-1-yl)-α-chloroacetamide.

20. Composition according to claim 11 wherein said compound is N-(tetrahydrofurfuryl)-N-(2,5-dimethyl-1-cyclopenten-1-yl)-α-chloroacetamide.

21. Method for selectively controlling undesirable plants associated with monocotyledonous and dicotyledonous crop plants which comprises applying to the locus thereof a herbicidally effective amount of a compound having the formula

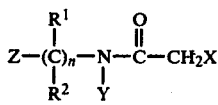

wherein
X is a halogen;
Y is a $C_{5-7}$ cycloalken-1-yl or cycloalkadienyl radical;
Z is a saturated or unsaturated heterocyclic radical having up to 6 ring atoms containing O;
n is 0, 1 or 2;
Y and Z may be unsubstituted or independently substituted with $C_{1-10}$ alkyl, $C_{2-8}$ alkenyl or alkynyl, $C_{1-8}$ alkoxy, $C_{2-12}$ alkoxyalkyl or polyalkoxy, $C_{5-7}$ cycloalkyl, cycloalkenyl or cycloalkadienyl, $C_{5-6}$ O-heterocyclyl, halogen, $NO_2$, $CF_3$, CN, OH, lower alkylthio, carboloweralkoxy, phenyl, benzyl or up to 4 carbon atom alkenylene or alkylene groups to form a ring therewith and
$R^1$ and $R^2$ are hydrogen or $C_{1-6}$ alkyl or alkenyl groups.

22. Method according to claim 21 wherein Y is a $C_{5-7}$ cycloalken-1-yl which may be substituted with any of said groups.

23. Method according to claim 22 wherein said cycloalken-1-yl is substituted with lower alkyl.

24. Method according to claim 23 wherein said alkyl-substituted cycloalken-1-yl is 2,6-di-loweralkylcyclohexen-1-yl.

25. Method according to claim 21 wherein n is 1 and Z is furyl.

26. Method according to claim 21 wherein n is 1 and Z is tetrahydrofuryl.

27. Method according to claim 26 wherein said compound is N-(furfuryl)-N-(2,6-dimethyl-1-cyclohexen-1-yl)-α-chloroacetamide.

28. Method according to claim 26 wherein said compound is N-(tetrahydrofurfuryl)-N-(2,6-dimethyl-1-cyclohexen-1-yl)-α-chloroacetamide.

29. Method according to claim 21 wherein said compound is N-(furfuryl)-N-(2,5-dimethyl-1-cyclopenten-1-yl)-α-chloroacetamide.

30. Method according to claim 21 wherein said compound is N-(tetrahydrofurfuryl)-N-(2,5-dimethyl-1-cyclopenten-1-yl)-α-chloroacetamide.

* * * * *